United States Patent
Cai et al.

(10) Patent No.: US 12,064,083 B2
(45) Date of Patent: Aug. 20, 2024

(54) REAL-TIME MEASUREMENT OF VISIBLE SURFACE AREA FROM COLONOSCOPY VIDEO

(71) Applicants: CARNEGIE MELLON UNIVERSITY, Pittsburgh, PA (US); ALLEGHENY SINGER RESEARCH INSTITUTE, Pittsburgh, PA (US)

(72) Inventors: Yang Cai, Pittsburgh, PA (US); Shyam Thakkar, Pittsburgh, PA (US)

(73) Assignees: CARNEGIE MELLON UNIVERSITY, Pittsburgh, PA (US); ALLEGHENY SINGER RESEARCH INSTITUTE, Pittsburgh (PA)

( * ) Notice: Subject to any disclaimer, the term of this patent is extended or adjusted under 35 U.S.C. 154(b) by 389 days.

(21) Appl. No.: 17/600,091

(22) PCT Filed: Apr. 2, 2020

(86) PCT No.: PCT/US2020/026305
§ 371 (c)(1),
(2) Date: Sep. 29, 2021

(87) PCT Pub. No.: WO2020/160567
PCT Pub. Date: Aug. 6, 2020

(65) Prior Publication Data
US 2022/0156936 A1    May 19, 2022

Related U.S. Application Data

(60) Provisional application No. 62/919,942, filed on Apr. 5, 2019.

(51) Int. Cl.
*G06T 7/00*   (2017.01)
*A61B 1/00*   (2006.01)
(Continued)

(52) U.S. Cl.
CPC ............ *A61B 1/00009* (2013.01); *A61B 1/31* (2013.01); *A61B 5/065* (2013.01); *A61B 5/6847* (2013.01);
(Continued)

(58) Field of Classification Search
CPC ..................... G06T 7/00; G06T 7/0014; G06T 2207/10068; G06T 2207/30168;
(Continued)

(56) References Cited

U.S. PATENT DOCUMENTS

| 7,894,648 B2 | 2/2011 | De Groen et al. |
| 8,064,666 B2 | 11/2011 | Bayer |

(Continued)

OTHER PUBLICATIONS

International Search Report and Written Opinion for International Patent Application No. PCT/US2020/026305 mailed on Jun. 24, 2020, 18 pages.

*Primary Examiner* — Tuan H Nguyen
(74) *Attorney, Agent, or Firm* — KDW Firm PLLC

(57) ABSTRACT

The present invention comprises a system and a computer-implemented method designed for measuring the visible colon surface area that has been seen from a colonoscope, and for displaying the results of the measurement. The method estimates the orientation of the camera of the colonoscope, estimates the travel distance of the scope camera from the axial vector lengths coming from or headed towards the focus of expansion point, and visualizing the percentage of the visible surface of the entire colon.

19 Claims, 16 Drawing Sheets

(51) Int. Cl.
*A61B 1/31* (2006.01)
*A61B 5/00* (2006.01)
*A61B 5/06* (2006.01)
*H04N 7/18* (2006.01)
*H04N 23/50* (2023.01)

(52) U.S. Cl.
CPC ........... *G06T 7/0014* (2013.01); *H04N 7/185* (2013.01); *G06T 2207/10068* (2013.01); *G06T 2207/30168* (2013.01); *H04N 23/555* (2023.01)

(58) Field of Classification Search
CPC ......... A61B 1/00; A61B 1/31; A61B 1/00009; A61B 5/065; A61B 5/6847; A61B 5/06; A61B 5/002; H04N 7/18; H04N 7/185; H04N 2005/2255
See application file for complete search history.

(56) References Cited

U.S. PATENT DOCUMENTS

| | | | |
|---|---|---|---|
| 2007/0135803 A1 | 6/2007 | Belson | |
| 2011/0242301 A1 | 10/2011 | Morita | |
| 2011/0251454 A1* | 10/2011 | Robb | A61B 5/064 |
| | | | 600/103 |
| 2015/0287243 A1* | 10/2015 | Itai | A61B 6/50 |
| | | | 345/419 |

* cited by examiner

REAL-TIME MEASUREMENT OF VISIBLE SURFACE AREA FROM COLONOSCOPY VIDEO

RELATED APPLICATIONS

This application is a national phase filing under 35 U.S.C. § 371 claiming the benefit of and priority to International Patent Application No. PCT/US2020/026305, filed on Apr. 2, 2020, which claims the benefit of U.S. Provisional Patent Application No. 62/919,942, filed Apr. 5, 2019. The contents of these applications are incorporated herein in their entireties.

BACKGROUND

Colon cancer is one of leading causes of cancer related deaths in the United States. Early colonoscopy diagnosis often leads to a complete cure and prevention of the deadly disease. Nearly all of colon cancers begin with noncancerous polyps (adenomas), which can gradually develop into colorectal cancer if they do not receive proper, timely treatment. Therefore, detecting and removing adenomas is a key to early diagnoses and prevention of colorectal cancer. However, missed adenomas during the colonoscopy procedure remains a significant problem.

Examination technique has been the most significant factor causing adenomas to be missed during the procedure. The variation in incidence rates suggests that quality control in colonoscopy remains a significant issue. As such, technological advances are needed to improve adenoma detection rates to reduce the incidence and mortality of colorectal cancer.

A colonoscopy is a therapeutic screening method for detecting non- or pre-cancerous polyps, colon cancers, and many other diseases. It is a manually-controlled endoscopic camera connected to a computer and a display. Currently, the procedures are performed based on visual observation and experience. A field survey found that the rate of missed polyps during the colonoscopy procedure can be as high as 28%. The scope moving speed, and the fatigue and vigilance of the practitioner play a significant role in the detection of polyps. In addition, the clarity of the colonoscopy video, the quality of the patient's preparation, and colon distention status are also measurable factors.

The most critical factor, however, is where the scope is aimed. To detect polyps, the scope first needs to be aimed in the right direction. A colon can be simplified as a cylinder having four quadrants. A well-trained practitioner will make sure all quadrants are thoroughly inspected. Therefore, the visible surface area is an essential measurement in the assessment of whether the operator has missed any quadrants during the screening process, normally during the scope withdrawal period. Additionally, it is beneficial to evaluate the colonoscopy procedure performance in real-time, when the colonoscope is still inside the patient's body, so that the practitioner can be notified that there are missing or under-examined areas which need to be revisited.

For over a decade, researchers have developed quantitative methods to evaluate the quality of exam (QoE) for colonoscopy procedures, including measuring, among other measures, the scope moving speed, scope rotational patterns, video clarity, preparation conditions. However, the visible surface measurement and comprehensive data visualization are still missing from this evaluation.

SUMMARY OF THE INVENTION

Described herein is a real-time, computer-assisted colonoscopy procedure performance quality measurement system which provides an evaluation using live or recorded colonoscopy videos. The system provides for an objective assessment of the colonoscopy. The system can be integrated into or added on to existing colonoscopy systems without modification. Additionally, it provides real-time feedback so that the practitioners can reassess areas of potential decreased visibility while performing the examination. The system can be used for quality assurance, training, and improvement of the polyp detection rate.

The system described herein is a system designed for measuring the visible colon surface area that has been seen from a colonoscope. This involves estimating the orientation of the scope camera, estimating the travel distance of the scope camera from the axial vector lengths coming or headed towards the Focus of Expansion (FOE) point, and visualizing the percentage of the visible surface of the entire colon.

A typical colonoscopy camera contains a wide-angle lens, a light, video feed, and control cables to manipulate the camera orientation: up, down, left and right. The average human colon is about 80 cm long. The colonoscopy screening procedure normally starts from the cecum (beginning of the colon) and the examination occurs as the colonoscope is withdrawn through the rectum. During the procedure, the practitioner looks for precancerous polyps and other pathologies on the wall of a colon, while controlling the orientation and moving speed of the camera. The process may also involve a biopsy, scope retroflexion, pumping water, injecting saline, polypectomy and other treatments.

As described herein, the normal exam motion is considered. If the colonoscopy video only contains a portion of the total wall area, say, only the top part of the wall, or 50% of the surface, then a determination is made that the exam has only covered 50% of the total surface at the length section. A partial surface inspection leads to the missed discovery of polyps and other symptoms on the wall of the colon.

For purposes of the present invention, the colon is divided into axial sections of a given length. The process comprises the following steps for each axial section of the colon. The camera orientation is first measured by detecting the vanishing point of the scope view to determine the quadrant of the colon wall to which the camera is aimed. The coverage percentage for that quadrant over the given length of the axial section is then calculated and the accumulated measurements for the section are updated. The process is repeated for each axial section until the colon exit is reached.

DETAILED DESCRIPTION

Figure 1:
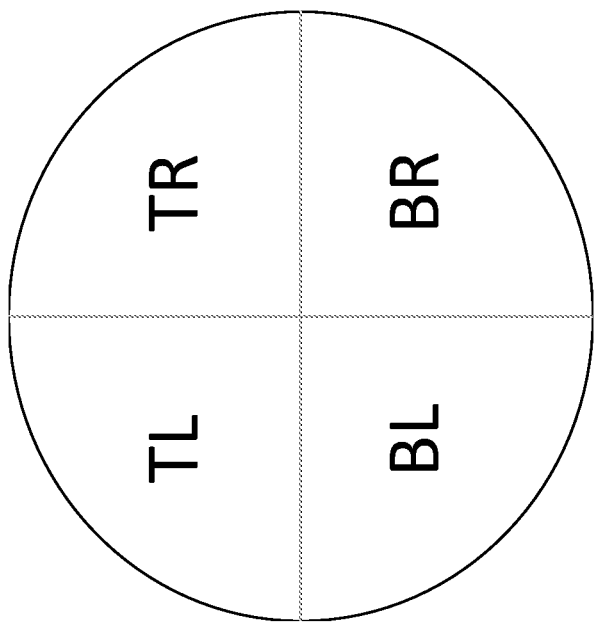
FIG. 1 shows an illustration of the wall of colon and four quadrants.

A colonoscopy camera can be controlled in four directions. The orientation of the camera can be determined from frames of the colonoscopy video. In a preferred embodiment of the present invention, the cross-section of the wall of the colon is divided into four quadrants: top left (TL), top right (TR), bottom left (BL) and bottom right (BR), as shown in FIG. 1. Although the invention is explained in terms of dividing the cross-section of the colon wall into quadrants, in alternate embodiments of the invention, the cross-section of the wall of the colon may be divided into more or fewer portions. The measurements per axial section of a given distance are calculated. In preferred embodiments, the axial sections of the colon are in the range of 5 cm-10 cm, but other lengths may be used in alternate embodiments. In the preferred embodiment, the measurement of interest to gauge examination coverage for each quadrant in each axial section is the number of frames of video captured in which each quadrant is visualized as the camera moves through the axial section.

The orientation of the scope camera, with respect to a given rotational position, can be used to gauge which quadrants are appearing in any given video frame. The number of frames in which a particular quadrant is visualized may be inferred as the number of frames in which the camera is oriented toward the quadrant. In some embodiments, a quadrant is determined to be visualized in the video frame if more than a certain percentage of the quadrant appears in the video frame.

Figure 2:
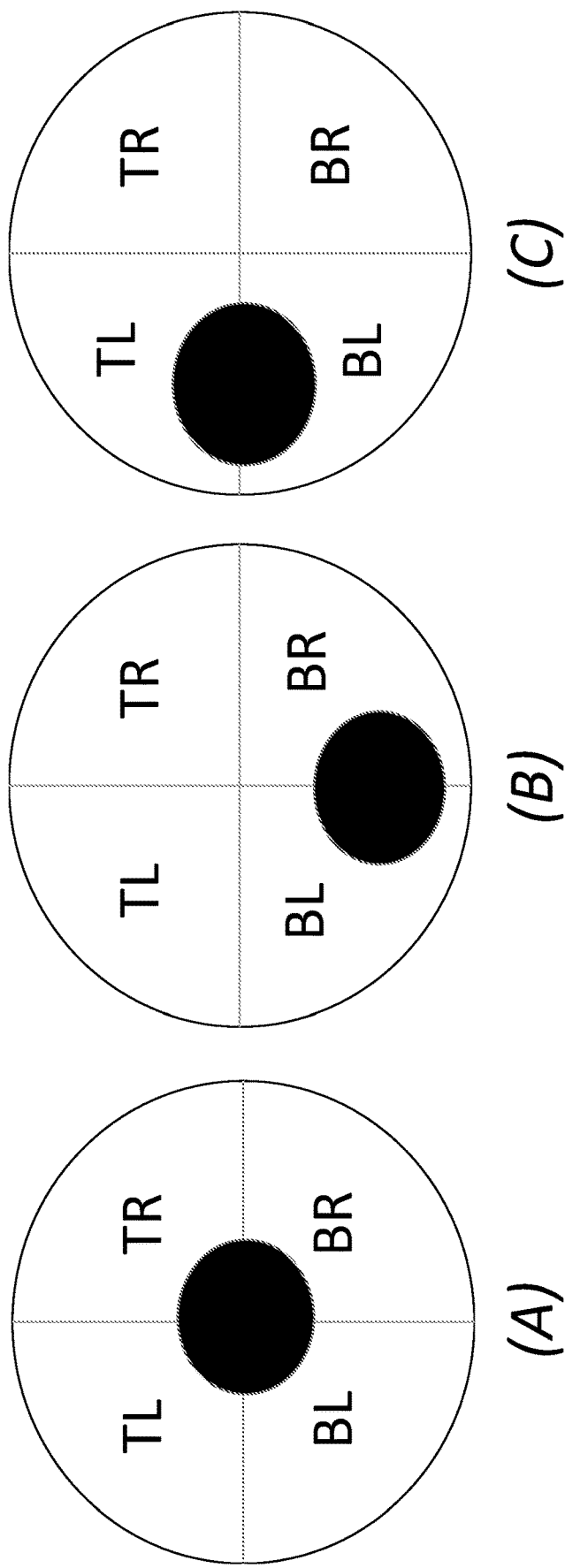
FIG. 2 shows the samples of the three cases of the locations of the shadow area (blob) and the camera orientations.

Estimating the orientation of the scope camera can be accomplished by determining shadow areas in each video frame. That is, quadrants containing shadow areas are determined. If the scope camera is aimed at the center of the colon, similar to a car traveling in a dark tunnel, a shadow area (dark blob) would be in the center of the image as the walls are on the side, whereby the operator can partially see all four quadrants. This is shown in idealized form in FIG. 2, View (A). If the camera is aimed to the top of the colon, then the shadow area would be in the bottom quadrants (BL and BR), indicating that the top left and top right quadrants are visualized in the video frame, as shown in FIG. 2, View (B). Likewise, if the camera is aimed to the right side of the colon, then the shadow area would be at the left side quadrants (TL and BL), indicating that the top right and bottom right quadrants are visualized in the video frame, as shown in FIG. 2, View (C).

Figure 3:
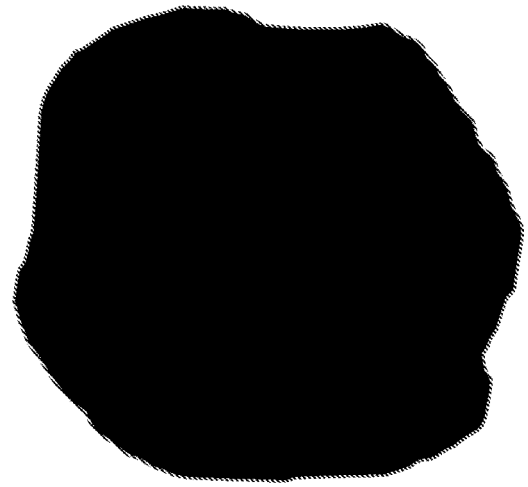
FIG. 3 shows the example of the shade filtering with closing operation and size threshold.
Figure 3:

The shadow area can be segmented using a pixel intensity level threshold after it is converted from a color image to a grey-scale one. The threshold can be adjusted based on the camera system, image resolution, and greyscale range. The shape of the shadow area (blob) can be further filtered by size, binary morphology, such as closing operation, and shape properties such as compactness, which is the ratio of the Area (A) to Perimeter (P): r=A/P. FIG. 3 shows an example of the shade filtering with closing operation and size threshold. View (A) is before filtering and View (B) is after filtering.

Estimating the scope travel distance is an important factor in the calculation of the overall coverage of the colon surface. In addition, the scope travel distance is necessary for determining when the end of an axial section has been reached. The scope travel distance can be obtained over time using optical flow and epi-polar plane projection. Based on the estimation of the scope's orientation and travel distance, the total percentage of the examined surface in the current axial section of the colon can be calculated.

Figure 4:
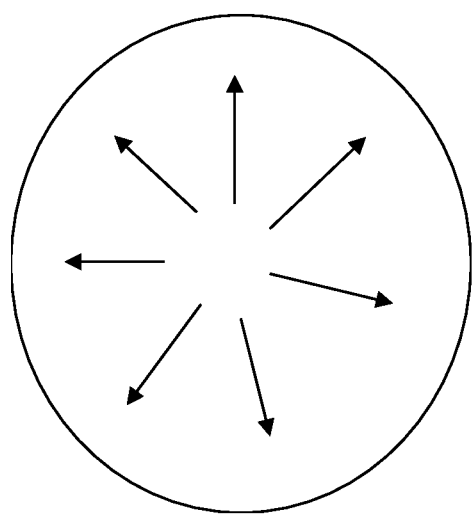
FIG. 4 shows examples of optical flow in different camera motions.
Figure 4:
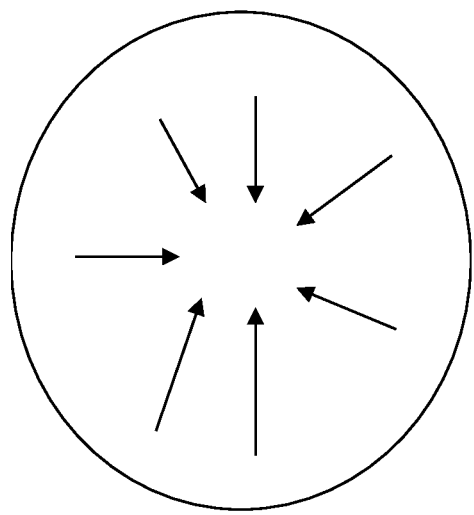
Figure 4:
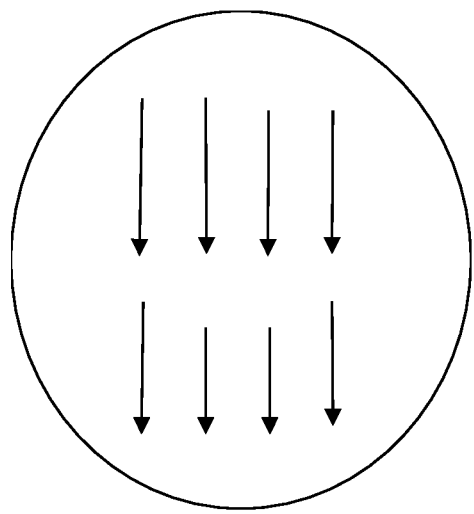
Figure 5:
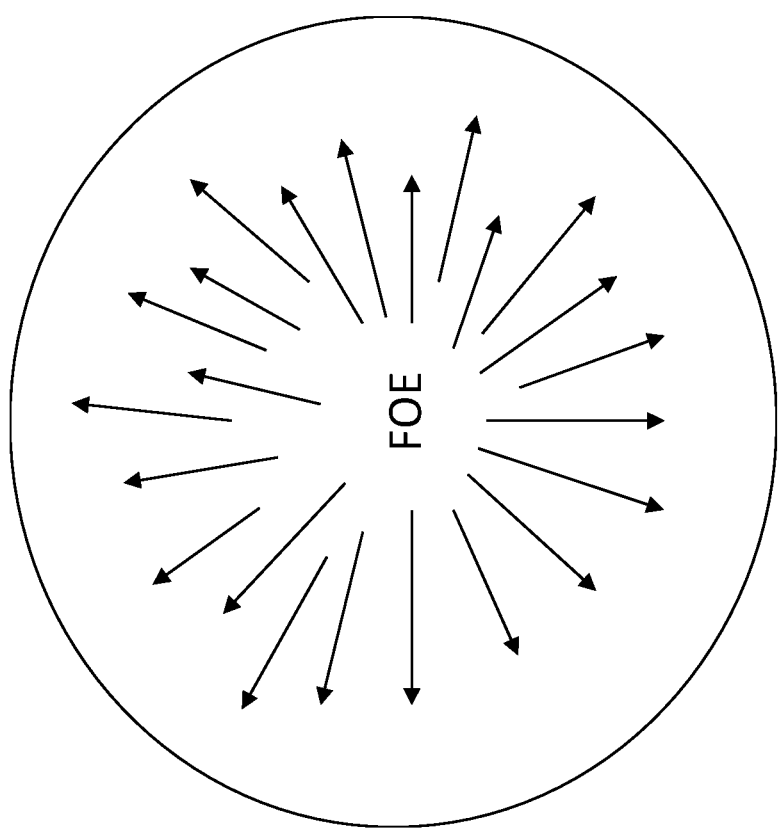
FIG. 5 shows example of Focus of Expansion.

The scope camera travel distance is estimated by the following process steps between each successive frames of the video: 1) calculating the optical flow which comprises a vector pattern caused by the relative motion between the camera and the surface from one frame to the next; 2) project the optical flow vectors to a two-dimensional image plane (i.e., an epi-polar plane); and 3) calculate the axial vector length coming or headed towards the Focus of Expansion (FOE) point. FIG. 4 shows examples of optical flow in different camera motions: moving in, in View (A), moving out, in View (B) and moving to right, in View (C). As would be realized by one of skill in the art, FIG. 4 shows only examples. The camera may move in any direction, creating many different vector patterns. FIG. 5 shows an example of FOE point.

Figure 6:
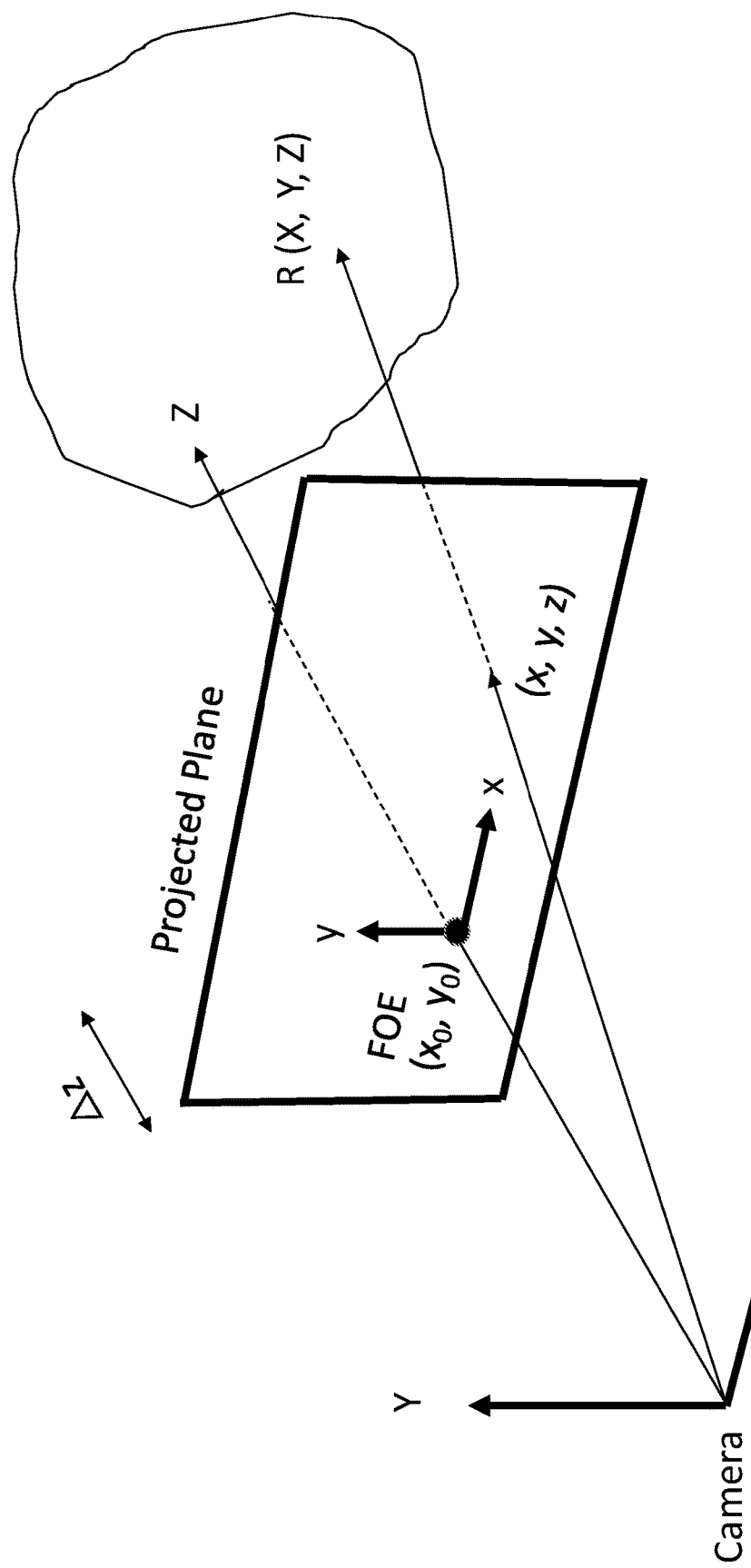
FIG. 6 illustrates the three-dimensional world points are projected to a two-dimensional image plane in video.

FIG. 6 illustrates the three-dimensional world points projected to a two-dimensional image plane in video. The basic assumption in this method is that illumination is consist during the optical flow calculation period. The light condition does not change. However, as the colon contains water and mucosal changes in some areas, the bright reflections might violate the illumination consistency assumption. In this case, an intensity filter can be applied to remove such anomalous spots. The basic optical flow calculation is based on following equation:

$$\frac{\partial I}{\partial x}V_x + \frac{\partial I}{\partial y}V_y + \frac{\partial I}{\partial t} = 0$$

where, $V_x$ and $V_y$ are x, y components of the optical flow of I(x,y,t) and $$\frac{\partial I}{\partial x}, \frac{\partial I}{\partial y}, \frac{\partial I}{\partial t}$$

are the derivatives of the image at (x,y,t) in the corresponding directions. There are many ways to solve the equation. In preferred embodiments of the invention, the Horn-Schunck computational approach is used, which generates global, intensive optical flow vectors.

Figure 7:
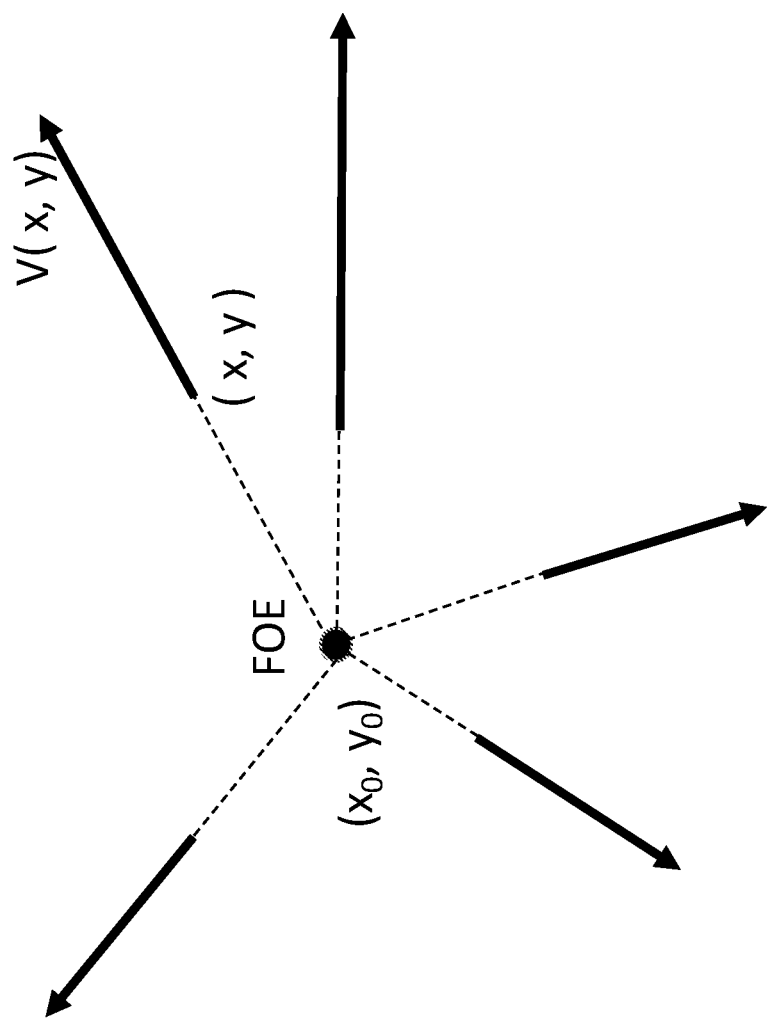
FIG. 7 illustrates the example of z towards the camera as the scope moves.

The FOE, as shown in FIG. 5, plays a critical role in the scope camera travel distance estimation. It is the intersection of the three-dimensional vector representation of the camera's translation direction and the projection plane. The coordinates of the FOE $(x_0, y_0)$ is the center of converging or diverging optical flow vectors.

$$(x_0, y_0) = \left(f\frac{x}{Z}, f\frac{y}{Z}\right)$$

where, f is the camera's focus distance, x and y are the projected coordinates of the world point $R \equiv (X,Y,Z)$. For z towards the camera (negative) the flow vectors point away from the FOE, indicating expansion, as shown in FIG. 4, View (A). For z away from the camera (positive) the flow vectors point towards the FOE, indicating contraction, as shown in FIG. 4, View (B). FIG. 7 illustrates the example of z towards the camera as the scope moves inwards.

With reference to FIG. 6, the projected plane is positioned at a distance f from the camera. The point R(X,Y,Z) has a projection p(x,y,z) on the projected plane at time T. The scope or the camera moves with a velocity $$\frac{\partial z}{\partial t}$$

over a distance $\Delta z = z' - z$, approaching the focus of expansion. At time T+1 the point p's new position will be at p'=(x',y',z'). From FIG. 6, the similar triangles of the projection lines when the plane moves back and forth can be seen. We have, $$\frac{y}{f} = \frac{Y}{Z} \text{ and } Y = \frac{yZ}{f}$$

$$\frac{\partial y}{\partial t} = f\left(\frac{\frac{\partial Y}{\partial t}}{Z}\right) - fY\left(\frac{\frac{\partial Z}{\partial t}}{Z^2}\right)$$

Because point R is fixed, set $$\frac{\partial Y}{\partial t} = 0.$$

We have, $$\frac{\partial y}{\partial t} = -yZ\left(\frac{\frac{\partial Z}{\partial t}}{Z^2}\right) = \frac{y}{Z}\left(\frac{\partial Z}{\partial t}\right)$$

$$\frac{y}{\frac{\partial y}{\partial t}} = -\frac{Z}{\frac{\partial Z}{\partial t}} = \tau$$

The value $\tau$ is known as the Time-To-Contact (TTC), which indicates the proportionality of the velocity of the optical flow vector projected to the plane on the y-axis to the velocity of the camera's motion toward the FOE. The representative value for r can be estimated as an average of the optical flow vectors, or, in alternate embodiments, the most likely value through machine learning using the optical flow vector pattern as an input. The ultimate value needs to be calibrated with a "ground truth", which can be, for example, a magnetic field positioning sensor, or the centimeter gap marks on the colonoscopy tube outside of the patient's body.

Note that there will be many axial vectors produced, each likely having a different magnitude and direction, indicating variances in speed and z-axis direction. For each successive frame, an additional axial vector will be calculated.

The scope travel distance can be obtained over time using the optical flow and epi-polar plane projection. The translation along the z direction of the scope, as indicated by each successive axial vector, and the associated coordinate system are used for estimating the scope travel in the video feed. Due to the latency of the 3D sensor (in some instances only updated every 3 seconds), the visual estimation is sensitive to changes. A low-pass filter can be used to smooth the estimation. The total distance travelled by the scope camera can be estimated by summing the plurality of axial vectors calculated for each successive video frame.

Based on the estimation of the scope's orientation and travel distance, the total percentage of the examined surface can be calculated. A counter for each quadrant in each axial segment of the colon counts in how many frames, in the axial segment, the particular quadrant has been visible in the video. For example, if the optimal number frames per segment is set to 500, then a count of 250 would be 50% coverage.

In summary, the algorithm needs no minimal feature points and is robust and fast enough for real-time processing. The initial tests on the real video clips showed the travel directions reflect the actual scope movements. For example, a positive value indicates moving in and a negative value indicates moving out. The actual centimeter output is also a feature.

Figure 8:
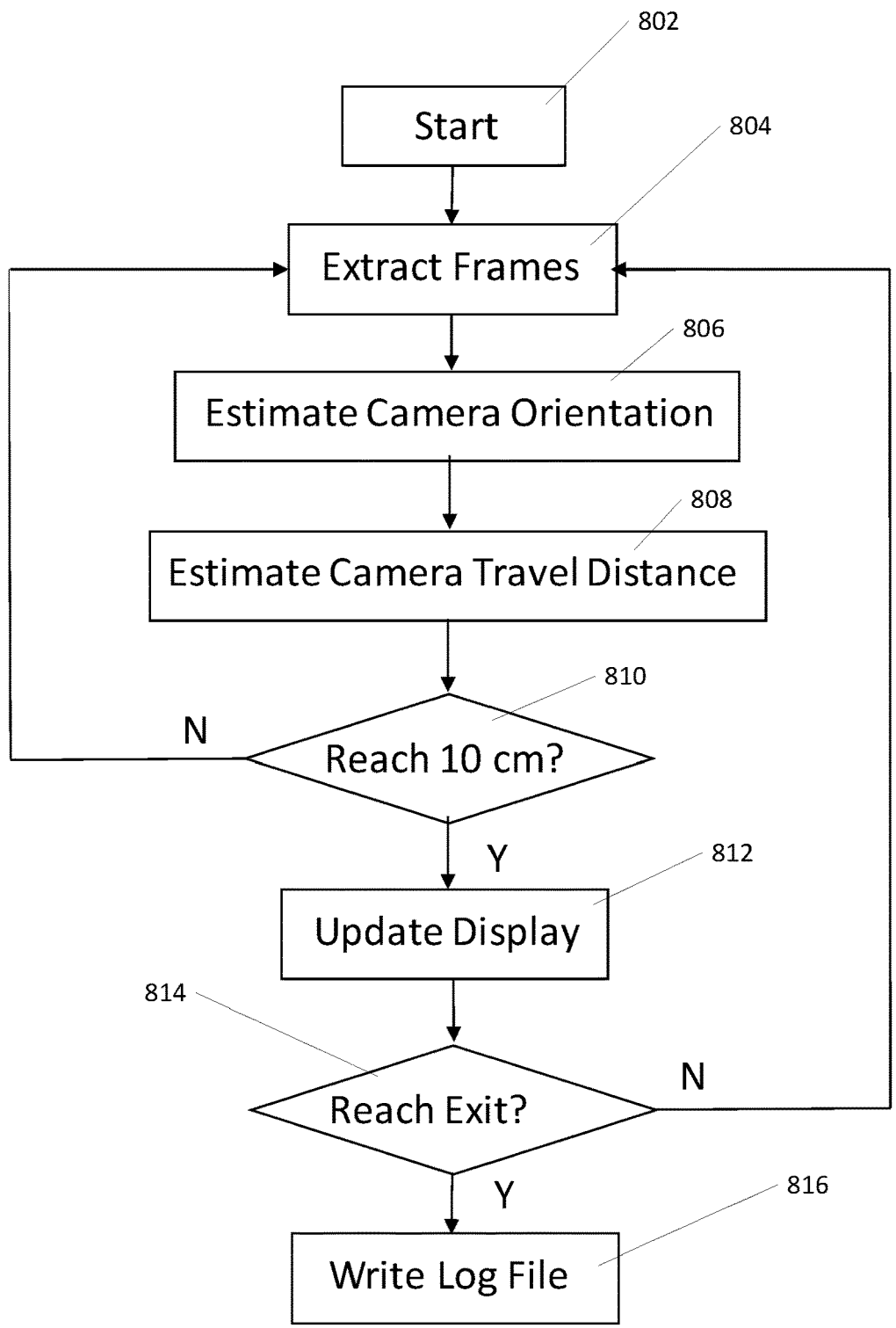
FIG. 8 is a flow chart showing the process flow.

FIG. 8 is a flowchart showing the process flow of the invention. The process starts at 802 wherein the camera probe was inserted into the colon of the subject. As the camera probe is withdrawn from the colon, frames are extracted from the recorded video at 804. At 806, the orientation of the camera is estimated. That is, an estimate is made as to which quadrant the camera is pointed. The frame count for the quadrant to which the camera is oriented is incremented, indicating that the frame extracted and 804 is a frame showing the wall of the colon in the quadrant to which the camera is estimated to be oriented. At 808, an estimate is made as to the distance that the camera has traveled, using the process described above. At 810, the is determined if the camera has been extracted far enough such that the scanning of the current actual segment is been completed. Although the flowchart shows an axial segment length of 10 cm, it will be realized in any length may be used for the axial segment. If the end of the axial segment has not been reached, control returns to 804 where another frame is extracted from the video. The process continues until the camera has been withdrawn far enough from the colon to reach the next axial segment.

Upon reaching the end of an axial segment at 810, the display is updated at 812. The updating of the display includes a visualization, as described below, which includes feedback for the practitioner regarding the coverage of each quadrant within each axial segment of the colon. At 814 is determined if the end of the colon has been reached. It should be noted that the final axial segment of the colon is likely to be less than the standard defined axial segment used in the 804-810 loop. If the end of the colon has not been reached in at 814, control returns to 804 or a frame is extracted for the next axial segment in the colon. If, at 814, the exit of the colon has been reached, a log file is written reflecting all results of the colonoscopy, including the coverage for each quadrant in each axial segment of the colon.

Figure 9:
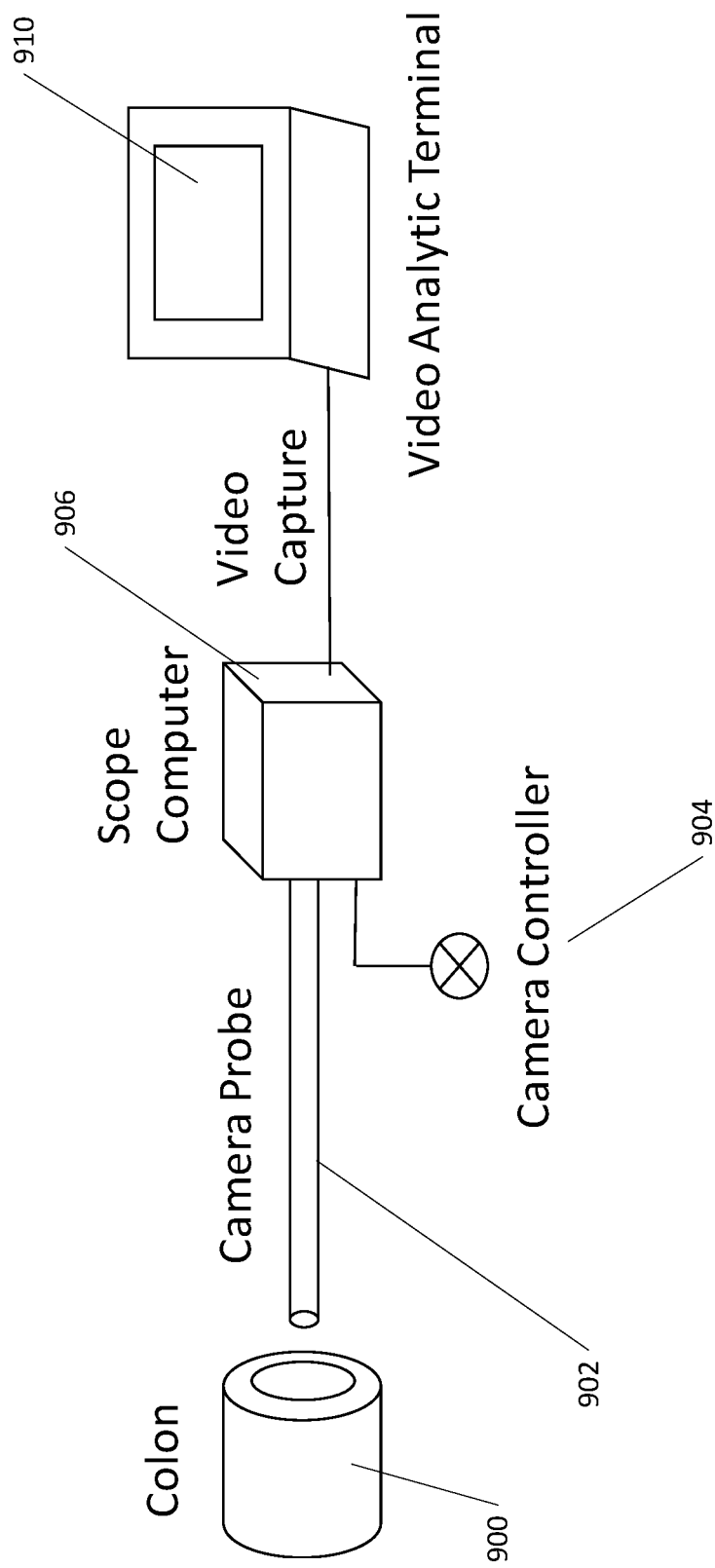
FIG. 9 is a diagram of the system.

FIG. 9 it is a diagram showing an exemplary embodiment of the system of the present invention. Reference 900 represents the colon of the subject. Camera probe 902 is inserted all the way into colon 900, and the visualization occurs as camera probe 902 is extracted from the colon. The orientation of the camera probe 902 within colon 900 is controlled by camera controller 904 under control of the practitioner performing the examination. Scope computer 906 processes the video captured by camera probe 900. Note that camera probe 902, camera controller 904 and scope computer 906 represent a standard set up used in traditional colonoscopy procedure.

The process of the present invention is executed on video analytic terminal 910. The process may be implemented as software implementing a computer-implemented method. The software may reside on a non-transitory computer-readable storage medium, and may be transferred to transitory memory, such as RAM, before being executed by a processor. Display of video analytic terminal 910 may be used to display the results of the analysis of the process of the present invention using a visualization as described below. The software preferably executes the process shown in flowchart form in FIG. 8, although variations of the process are contemplated to be within the scope of the invention. The log file created in step 816 of the process shown in FIG. 8 may be stored on a non-transitory computer-readable storage medium in video analytic terminal 910. Video analytic terminal 910 may include a network connection which may be used to extract log files or to update system software or the software implementing the present invention. Video analytic terminal 910 also includes a connection to scope computer 906, which may be a network connection, or a wired connection, for example, a USB connection or any other known format of wired connection.

Video analytic terminal 910 may be, for example, desktop computer, laptop computer, tablet computer, or any other computer capable of interfacing with scope computer 906 and executing the software in permitting the present invention. Video analytic terminal 910 should include a processor, transitory memory from which software may be executed, as well as a non-transitory, computer-readable storage medium for the permanent storage of software and log files. Video analytic terminal 910 should also include one or more means of communicating with other devices, for example, network connection, USB connection, or any other type of connection now known or later developed.

Visualization

Another novel aspect of the invention is the method of visualizing the results. The coverage of each quadrant in each axial segment of the colon can be visualized such as to provide real-time feedback to the practitioner. The real-time visualization provides the advantage of being able to go back and re-do quadrants that have been given less than optimal coverage.

The surface of the interior of the colon can be visualized as an array of 4×n cells, where 4 rows represent 4 quadrants and n columns represent n axial segments of the walls of the colon. As will be realized, the number of columns will vary, depending on the length of the colon. A cursor within a segment indicates the current scope location. An exemplary visualization using the surface map is shown in FIG. 10.

The percentage value of coverage is mapped to a color heat map. For example, if the coverage is zero percent for a quadrant, then the cell color for that quadrant may be black (e.g., an intensity level of 0). If the coverage is 100%, then the color may be white or green (e.g. an intensity level is 255). As should be realized, any colors may be used to represent various percentages of coverage. Preferably, the colors will be contrasting so as to alert the practitioner to less than 100% coverage of any given segment of the colon.

Figure 10:
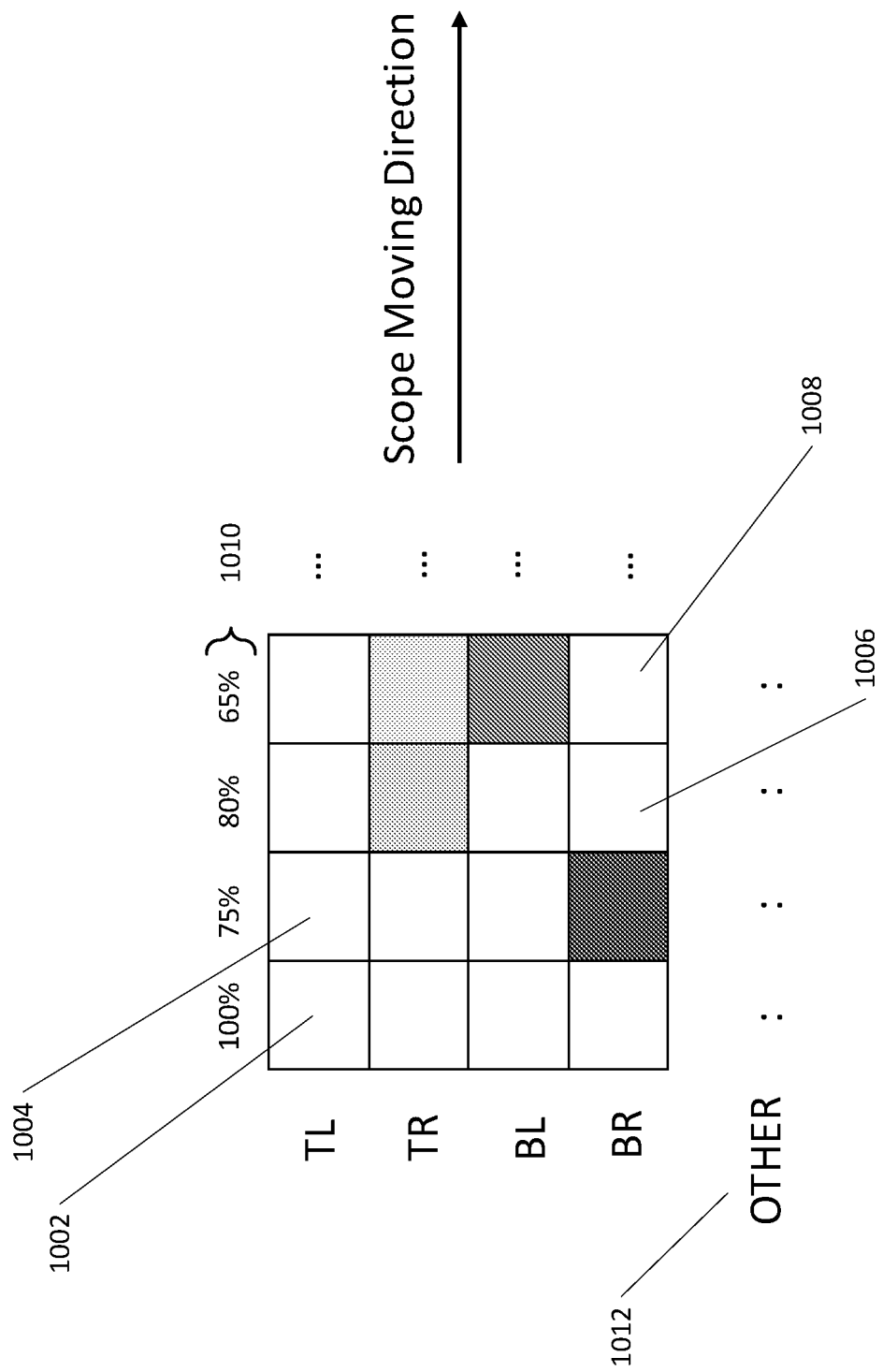
FIG. 10 is an exemplary display of the visualization of the surface map and measurement results.

As an example, reference number 1002 in FIG. 10 shows a column wherein all quadrants have at or near 100% coverage, as indicated by the white squares. Column 1004 in FIG. 10 indicates that the top left, top right and bottom left quadrant all have at or near 100% coverage, but that the bottom right quadrant has been missed. Column 1006 in FIG. 10 indicates at the top left quadrant, the bottom left cloud quadrant and the bottom right quadrant all have at or near 100% coverage but that the top right quadrant has only partial coverage as indicated by the gray square. It can be assumed that the coverage for the top right quadrant of column 1006 is around 20%. Column 1008 in FIG. 10 shows that the top left and bottom right quadrants have at or near 100% coverage but that the top right quadrant and the bottom left quadrant have not been completely covered. The lighter color of the cell representing the top right quadrant in column 808 indicates a higher percentage of coverage than the darker color of the cell representing the bottom left quadrant in column 1008.

Figure 16:
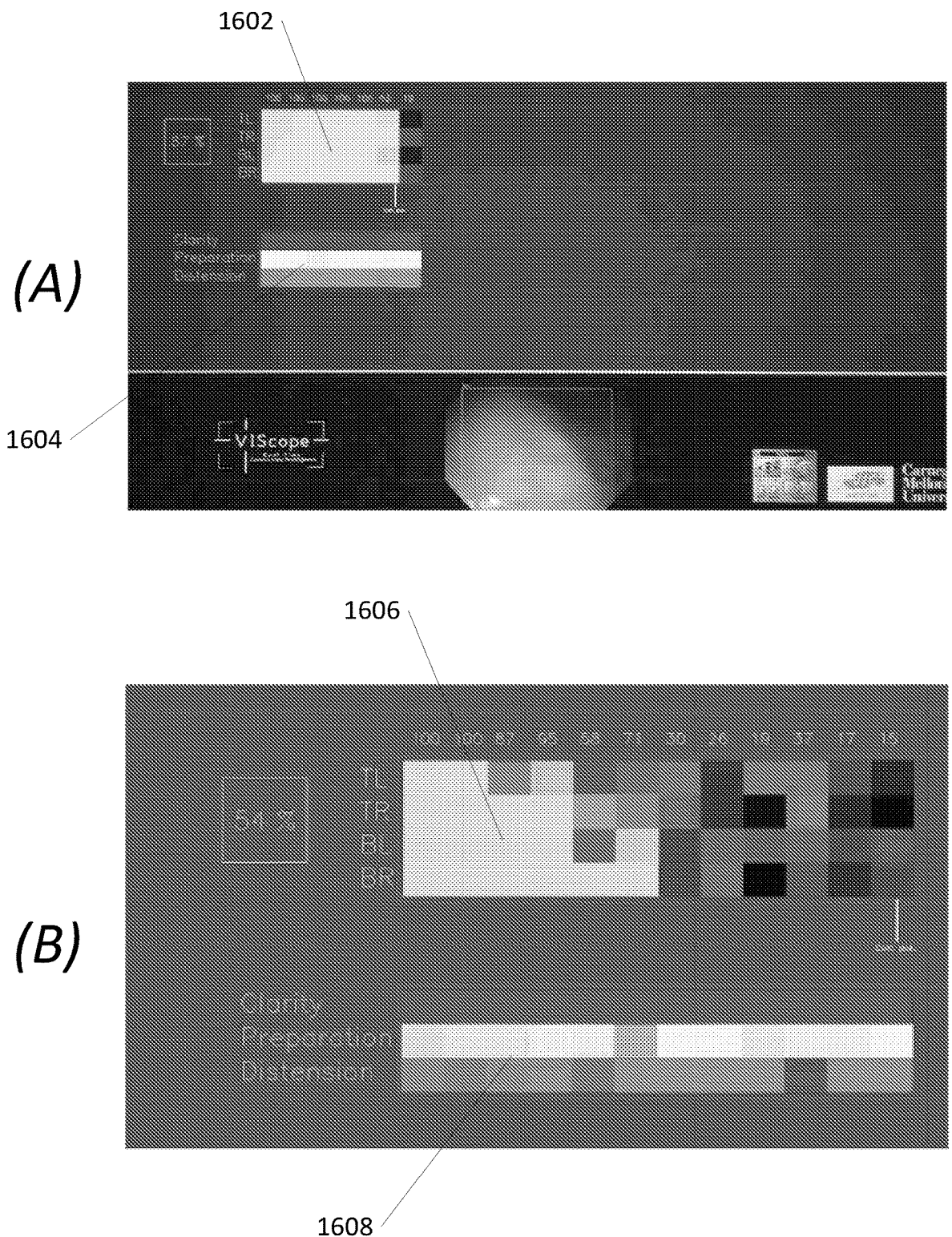
FIG. 16 shows examples of the display of the video analytic terminal of the invention showing visualization of the surface map and an example of the extension of the service map to include other measurements.

FIG. 16, shows two examples of the surface map visualizations as reference number 1602 in View (A) and as reference number 1606 in View (B).

In some embodiments, the visualization may include percentages 1008 for each column, representing the overall coverage percentage for each axial section of the colon.

In yet other embodiments, the total examined surface map cells can be expanded to display other measurements 1012, such as video clarity, preparation conditions, and distention level, etc. Clarity is a measurement of the image quality of the video, which is a measurement of blurriness with a Gaussian Function. Preparation is a measurement of the existence of food, colored drink, or stool, which can be recognized by a color vision model. Distention is a measurement of expansion of the diameter of a colon when it is inflated, typically by pumping air or carbon dioxide into the colon, which is described by a shape model. Those measurements can be mapped into additional cells below the surface map, with the same scope location cursor and columns. The multiple measurement maps can be updated in real-time and exported into a log file after the procedure in an XML format.

FIG. 16 shows two examples of the surface mapping visualization being extended to show other measurements, in this case, clarity, preparation and distention, as reference number 1604 in View (A) and as reference number 1608 in View (B).

Comparison With Manual Methods

Figure 11:
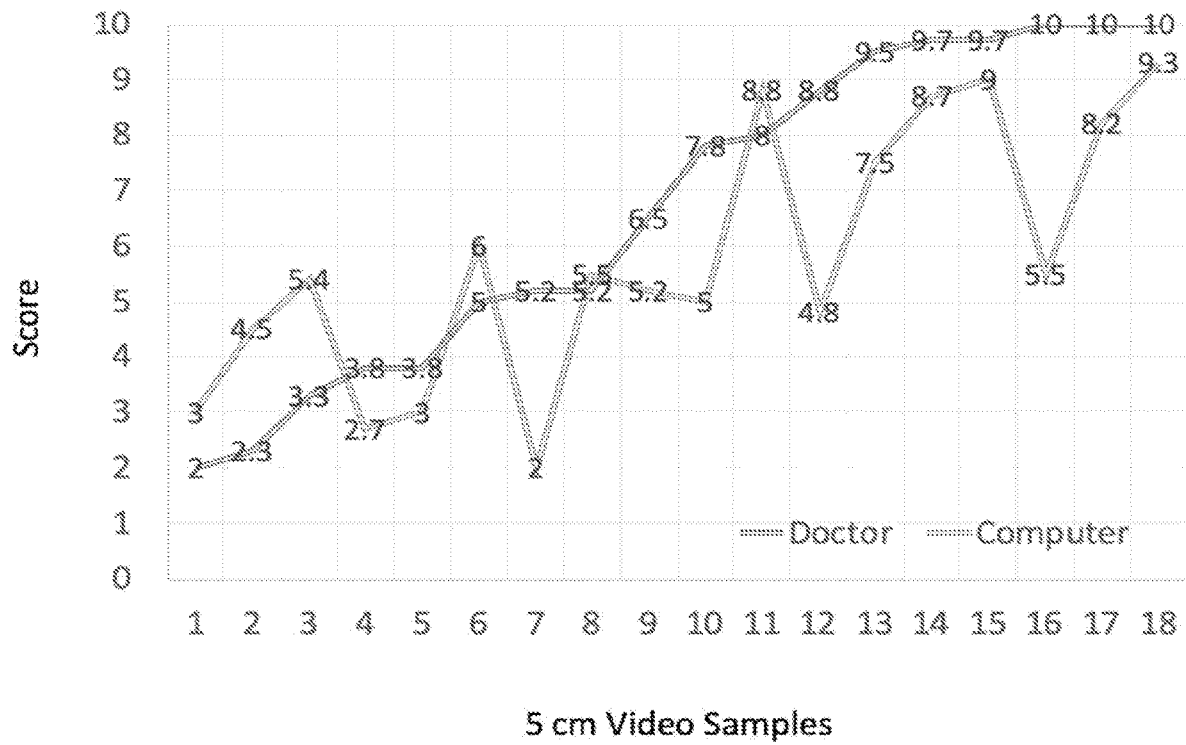
FIG. 11 is a graph showing a comparison between an evaluation of the coverage of the surface area of each quadrant of the wall of made by a practitioner and by the present invention.

In the surface area evaluation, the software calculates the result of visibility of four quadrants every 5 cm. FIG. 11 shows a comparison of the overall average evaluation of surface area of the practitioner versus the present invention. Here, a correlation of around 76% was found. When the practitioner was asked to repeat the evaluation, it was found that the computer's results appear to be more consistent than humans.

Figure 12:
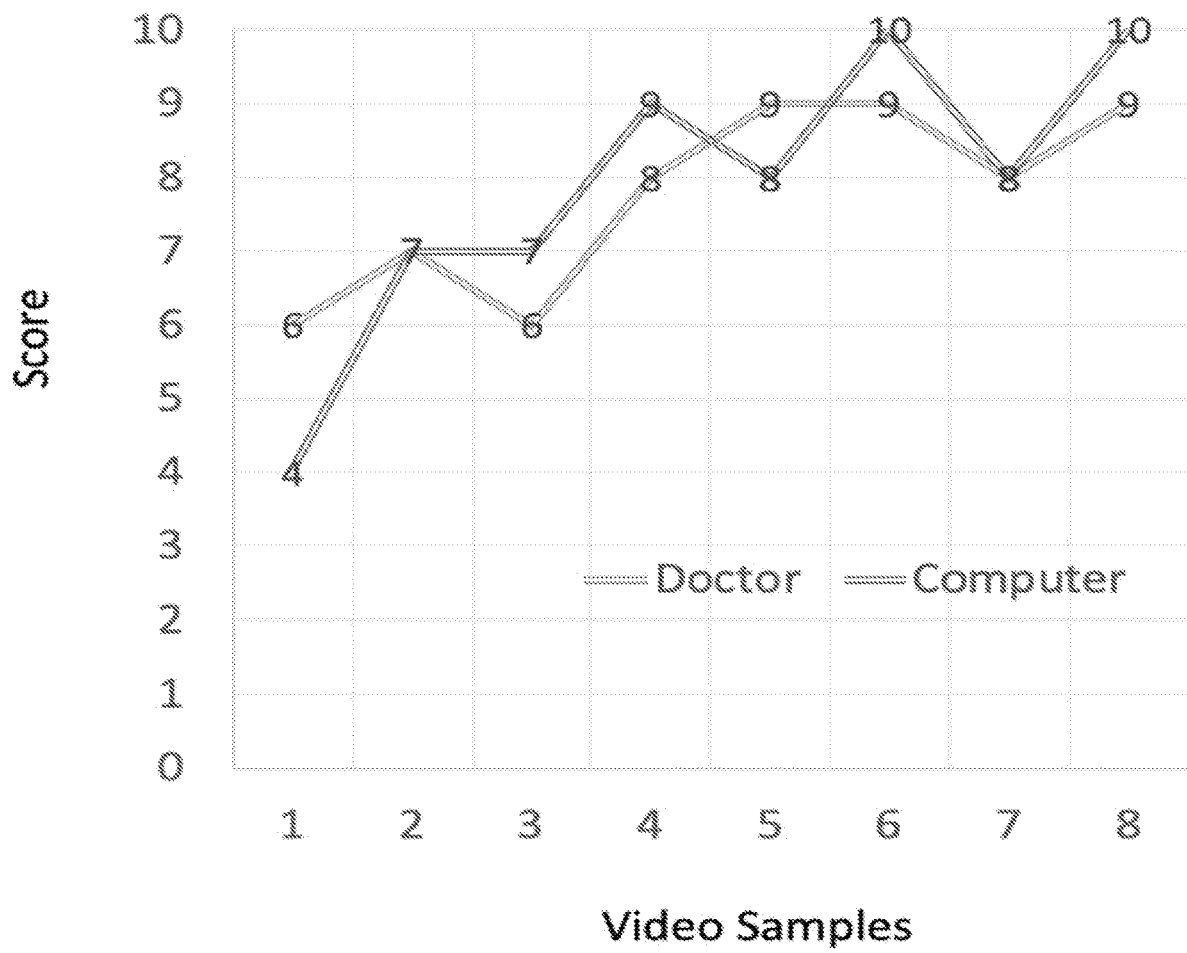
FIG. 12 is a graph showing a comparison between an evaluation of the clarity of the video made by a practitioner and by the present invention.

Clarity is evaluated based upon how and evaluation of the video quality compares from that of the practitioner and that of the computer. Eight videos were used to evaluate the software on clarity. FIG. 12 shows a comparison between the practitioner and the present invention. The correlation between the practitioner and the present invention was found to be 83.9%.

Figure 13:
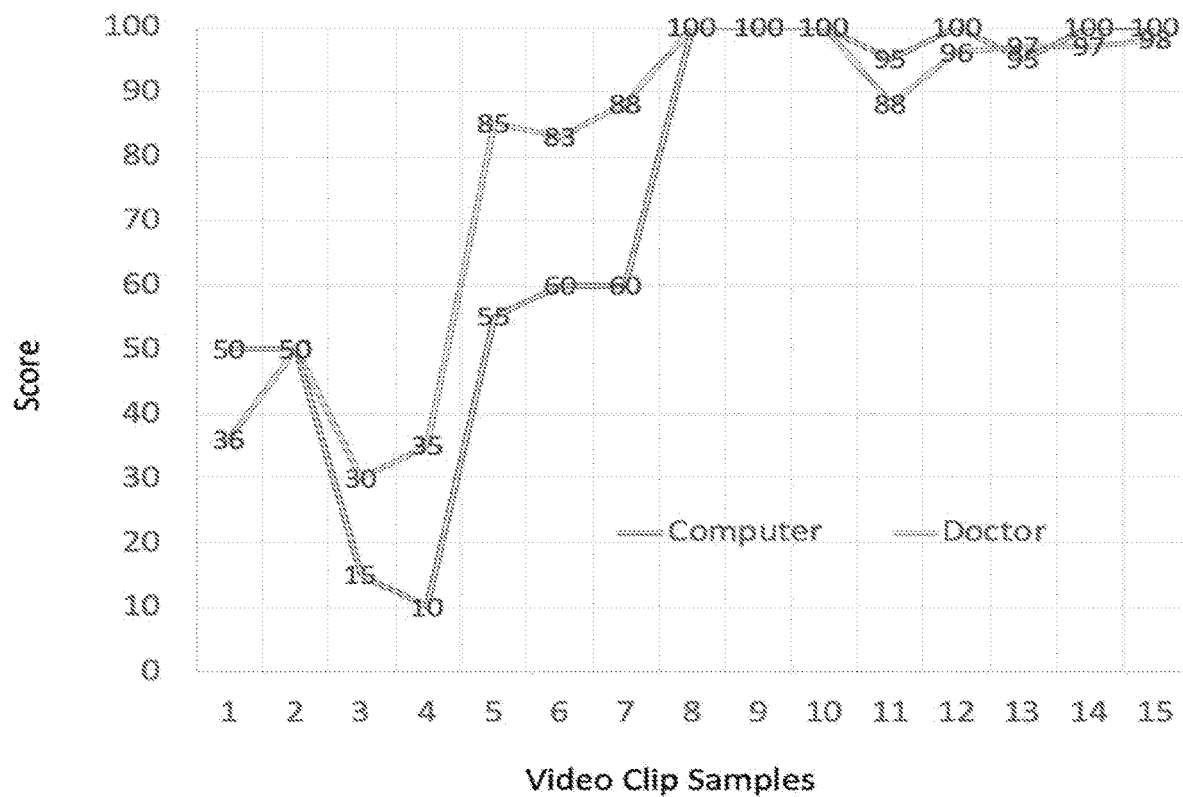
FIG. 13 is a graph showing estimates of the quality of the subject's preparation for the procedure, as indicated by the presence of stool in a video frame, made by the present invention and the practitioner.

FIG. 13 is a graph showing comparisons of estimates of the quality of the subject's preparation for the procedure made by the present invention and the practitioner. The preparation condition refers to the detection of stool in a given frame. The videos were scored from 0% to 100%, and it was found that the correlation between the practitioner and the present invention was approximately 90%. This indicates that the computer results are consistent with the expert's assessment.

Figure 14:
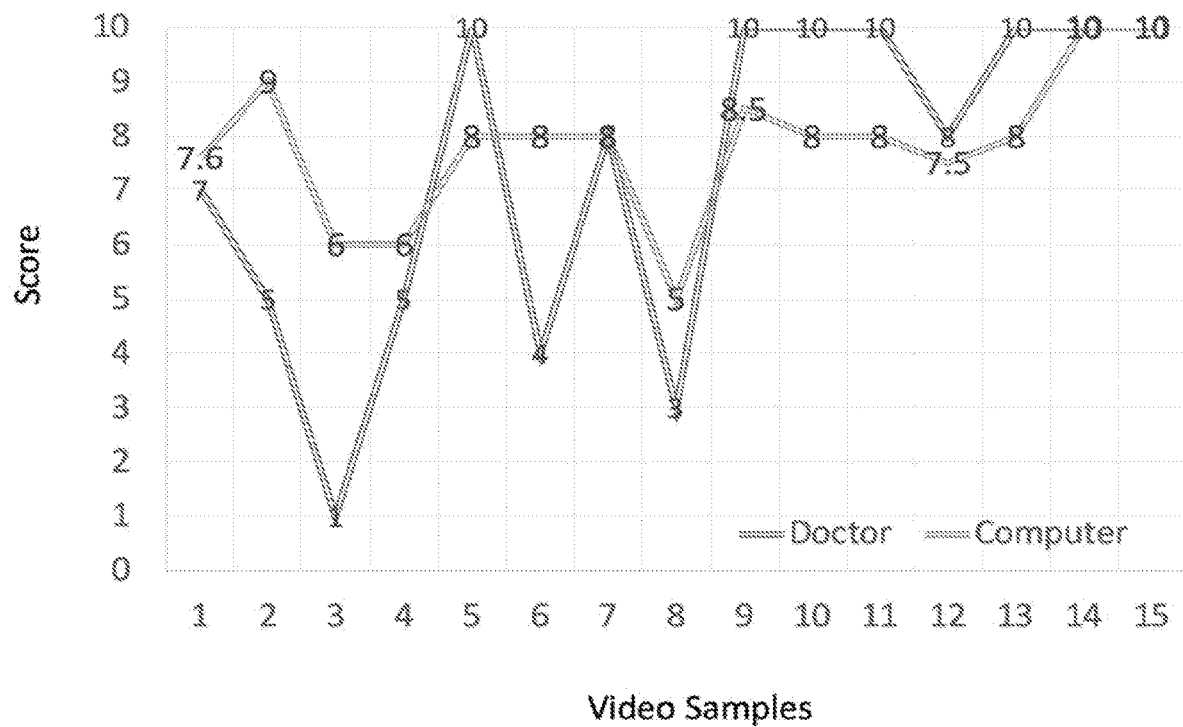
FIG. 14 is a graph showing comparison between estimates of the distention calculation, based upon the shape of the cross-section of folds in a given part of the colon, made the present invention and by a practitioner.

Distension calculation is based upon the shape of the cross-section of folds in a given part of the colon. FIG. 14 shows a comparison of the calculation made by the practitioner and by the present invention. The correlation between the practitioner and the present invention was found to be about 67.9%. The results show that there is room for improvement in the shape classification algorithm, especially in some anomalous cases. An example would be video segment 3, where the practitioner scores only 1 but the computer scores 6.

Figure 15:
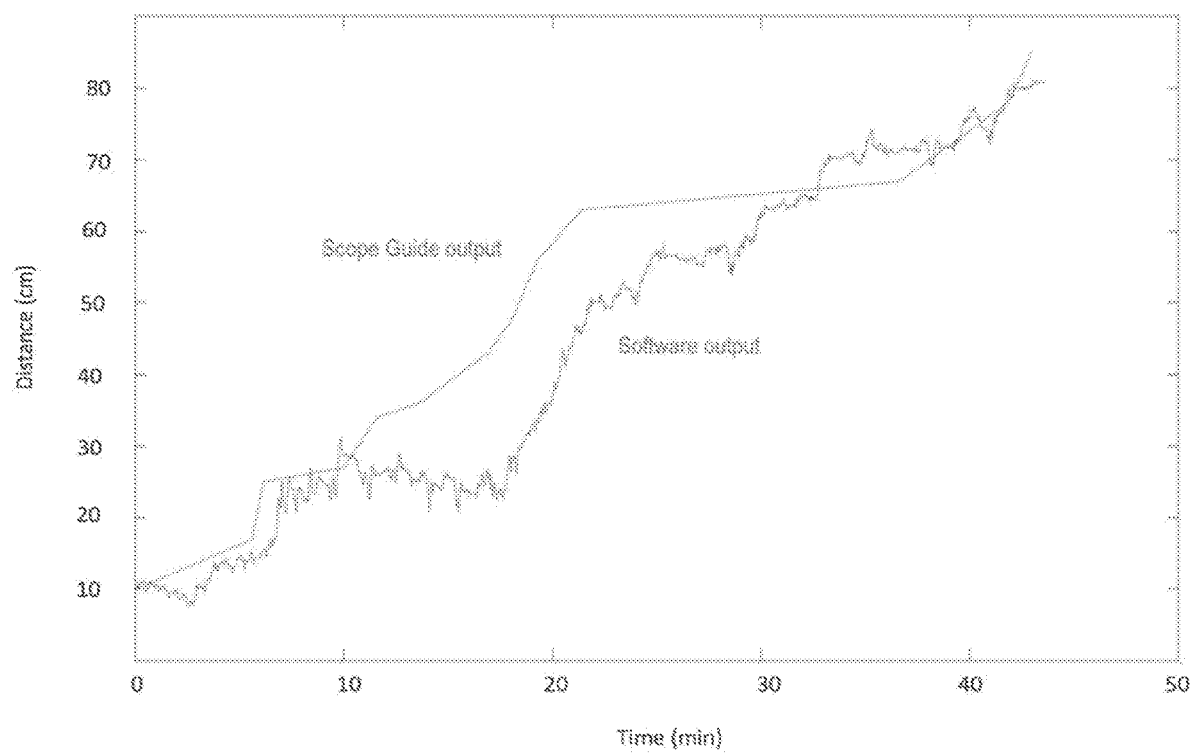
FIG. 15 is a graph showing a comparison of an estimation of the scope travel distance in the colon made by the present invention and by a commercially-available position sensor.

Lastly, the computer's estimation of the distance that the scope has travelled within the colon result was compared with a commercially-available position sensor in real-time and the data from both systems was recorded and is displayed in the graph in FIG. 15. It was found that the system of the present invention has a much faster tracking response time (30 frames per second) than the Scope Guide (less than 1 frame per second). Therefore, system of the present invention can reveal more dynamic information than the existing equipment. In addition, the invention can provide the scope orientation at the quadrant level, whereas the Scope Guide cannot.

The system of the present invention was tested at an endoscopy laboratory. FIG. 16, View (A) shows a screenshot of the system in normal operation conditions. The visualization shows that the colonoscopy procedure was going well and most scores were perfect. FIG. 16, View (B) shows an anomalous situation in which the scope cable broke down and failed to tilt its head around. The visible surface area measurement 1604 shows high percentages of missing areas. This kind of incident only rarely happens, but it serves to show how the visualization indicates quadrants having less than perfect coverage.

The present invention comprises a real-time video analytics system for measuring colonoscopy performance. The quality of exam evaluation includes the estimation of total visible surface areas per segment, real-time feedback to the endoscopist of areas visualized, and a color-coded display demonstrating exam quality in real-time for clarity, preparation conditions, and distention conditions.

Laboratory experiments show that the correlations between the computer and the experienced practitioner are: 76% in visible surface area estimation, 83.9% in clarity evaluation, 90% in preparation condition assessment, and 67.9% in distention condition evaluation. The algorithm has been shown to be faster in response to dynamic scope movements compared to a 3D scope positioning device. In addition, the clinical experiment shows the system detected unexpected scope malfunction events in real-time.

The invention has been described with reference to specific embodiments. It should be realized by one of skill in the art that variations can be made to the described embodiments while remaining within the contemplated scope of the invention, which is specified by the claims which follow.

We claim:
1. A computer-implemented method comprising:
   dividing a colon into axial sections of a given length;
   dividing each axial section into a plurality of cross-sectional portions;
   for each frame of video extracted from a camera as the camera is moved through each axial section:
      determining to which cross-sectional portion of the axial section the camera is oriented in the video frame;
      incrementing a counter for the cross-sectional portion to which the camera is oriented;
      comparing the counter for each cross-sectional portion to an optimal value; and
         visualizing the variance of the counter from the optimal value for each cross-sectional portion.
2. The method of claim 1 wherein the cross-sectional portions are quadrants.
3. The method of claim 1 wherein the cross-sectional portion of the axial section to which the camera is oriented is determined by a shadow area in the extracted video frame.
4. The method of claim 3 wherein the cross-sectional portion to which the camera is oriented is the cross-sectional opposite the cross-sectional portions containing the shadow area.
5. The method of claim 3 wherein the shape of the shadow area in the extracted frame is filtered with area size, compactness, and closing operation.
6. The method of claim 1, further comprising:
   determining that the end of an axial section has been reached by estimating the distance that the camera has moved through the axial section and comparing it with the given length of the axial section.
7. The method of claim 6 wherein estimating the distance that the camera has moved through the axial section between frames comprises:
   calculating an optical flow comprising a vector pattern caused by relative motion between the camera and an interior surface of the colon as determined from successive extracted video frames;
   projecting the vector pattern to an epi-polar plane; and
   calculating an axial vector based on the projected vector pattern with respect to a focus of expansion.
8. The method of claim 7 wherein the axial travel direction of the camera is determined from the direction of the optical flow vectors with respect to the focus of expansion.
9. The method of claim 7 wherein the speed of the camera as it moves through the axial section is given by the magnitude of the axial vector.
10. The method of claim 1 wherein the visualization comprises, for each cross-sectional portion in each axial section, a cell comprising a heat map indicating the variance of the counter for each cross-sectional portion.
11. The method of claim 1 wherein the cells for each cross-sectional portion are arranged in a matrix of color rectangles wherein the rows of the matrix indicate the cross-sectional portions and the columns of the matrix indicate the axial sections.
12. The method of claim 11 wherein additional rows in the matrix include information regarding other measurements for each axial section.
13. The method of claim 12 wherein the other measurements include a clarity score, a colonoscopy preparation score, and a colon distention score.
14. An apparatus comprising:
   a camera mounted on an endoscope;
   a camera controller for controlling the orientation of the camera;

a scope computer connected to the endoscope and the camera controller for collecting video captured by the camera and for relaying control signals from the camera controller to the endoscope; and a video analytic computer, coupled to the scope computer and receiving video captured by the camera from the scope computer, the video analytic computer executing software for performing the functions of:

dividing a colon into axial sections of a given length;

dividing each axial section into a plurality of cross-sectional portions;

for each axial section:

for each frame extracted from the video as the endoscope is moved through the axial section:

determining to which cross-sectional portion of the axial section the camera is oriented in the video frame; and incrementing a counter for the cross-sectional portion to which the camera is oriented;

when the camera has moved to the end of the axial section:

comparing the counter for each cross-sectional portion to an optimal value; and visualizing the variance of the counter from the optimal value for each cross-sectional portion.

15. The apparatus of claim 14 wherein the cross-sectional portion of the axial section to which the camera is oriented is determined by a shadow area in the extracted video frame, wherein the cross-sectional portion to which the camera is oriented is the cross-sectional portion opposite the cross-sectional portion containing the shadow area.

16. The apparatus of claim 14, wherein software performs the further functions of:

determining that the end of an axial section has been reached by estimating the distance that the camera has moved through the axial section and comparing it with the given length of the axial section, wherein estimating the distance that the camera has moved through the axial section between frames comprises:

calculating an optical flow comprising a vector pattern caused by relative motion between the camera and an interior surface of the colon as determined from successive extracted video frames;

projecting the vector pattern to an epi-polar plane; and calculating an axial vector based on the projected vector pattern with respect to a focus of expansion.

17. The apparatus of claim 16 wherein the axial travel direction of the camera is determined from the direction of the optical flow vectors with respect to the focus of expansion and wherein the speed of the camera as it moves through the axial section is given by the magnitude of the axial vector.

18. The apparatus of claim 14 wherein the visualization comprises, for each cross-sectional portion in each axial section, a cell comprising a heat map indicating the variance of the counter for each cross-sectional portion, wherein the cells are arranged in a matrix of color rectangles wherein the rows of the matrix indicate the cross-sectional portions and the columns of the matrix indicate the axial sections.

19. The apparatus of claim 18 wherein additional rows in the matrix include information regarding other measurements for each axial section, wherein the other measurements include a clarity score, a colonoscopy preparation score, and a colon distention score.

* * * * *